United States Patent [19]

Bright et al.

[11] 4,233,458

[45] Nov. 11, 1980

[54] PROCESS FOR PREPARING N,N-DIMETHYLAMINOBENZOIC ACIDS

[75] Inventors: John H. Bright, Kendall Park, N.J.; Joseph L. Schmitt, Jr., Bethel, Conn.

[73] Assignee: American Cyanamid Company, Stamford, Conn.

[21] Appl. No.: 928,950

[22] Filed: Jul. 28, 1978

[51] Int. Cl.³ .............................................. C07C 99/00
[52] U.S. Cl. .................................................... 562/458
[58] Field of Search ................. 260/580; 562/419, 458

[56] References Cited

U.S. PATENT DOCUMENTS

| | | | |
|---|---|---|---|
| 3,324,175 | 6/1967 | Mallonee | 562/458 |
| 3,499,034 | 3/1970 | Gonzaley | 260/580 |
| 3,882,171 | 5/1975 | Levy | 562/458 |
| 3,931,210 | 1/1976 | Zenget et al. | 562/458 |
| 3,935,264 | 1/1976 | Bhutani | 260/580 |

OTHER PUBLICATIONS

Pearson et al., J.A.C.S., vol. 73, p. 864 (1951).
Adams et al., J.A.C.S., vol. 49, pp. 1093–1099 (1927).
Shmonina et al., Chem. Abst., vol. 50, #12618g (1956).
Bowman et al., J. Chem. Soc., pp. 1342–1348 (1950).

*Primary Examiner*—Bernard Helfin
*Assistant Examiner*—James H. Reamer
*Attorney, Agent, or Firm*—Bruce F. Jacobs

[57] ABSTRACT

N,N-Dimethylaminobenzoic acids are prepared by a two-step process of reductively alkylating nitrobenzoic acid in methanol in the presence of a palladium catalyst.

10 Claims, No Drawings

PROCESS FOR PREPARING N,N-DIMETHYLAMINOBENZOIC ACIDS

This invention relates to an improved process for the manufacture of N,N-dimethylaminobenzoic acids, particularly 3-dimethylaminobenzoic acid, by a two-step reductive alkylation in methanol in the presence of a palladium catalyst.

3-Dimethylaminobenzoic acid is an intermediate used in the manufacture of Crystal Violet Lactone, which in turn is an important color former compound used in the preparation of carbonless carbon paper.

Dimethylaminobenzoic acids have been prepared by various investigators, but in practice the procedures generally have not been practical or have had certain inherent deficiencies. Bowman and Stroud, J. Chem. Soc. 1950, p. 1342, dimethylated the isomeric aminobenzoic acids by reacting them with formaldehyde in acetic acid solvent at room temperature in the presence of palladised charcoal. It was found that the reactions could not be conducted in either ethanol or aqueous ethanol because of the separation of a resinuous mass, presumably the methylene derivative, which enclosed the catalyst and prevented further reduction from proceeding. 2-Nitrobenzoic acid was dimethylated in acetic acid in 13 hours using 36 percent of a 10% palladium-on-carbon catalyst (3.6% palladium, based on the weight of 2-nitrobenzoic acid) and gross amounts of formaldehyde.

Pearson et al., J. Am. Chem. Soc. 73, 864 (1951) stressed stoichiometric amounts of formaldehyde and conducted the reaction in 95% ethanol and 5 ml. concentrated hydrochloric acid based on the substrate and gross amounts of pre-reduced Adams catalyst (platinum). This procedure, in addition to the use of large amounts of catalyst, is complicated by the presence of hydrochloric acid during isolation.

The presently available methods for the preparation of 3-dimethylaminobenzoic acid are not satisfactory because they are ineffecient (use gross amounts of catalyst and/or formaldehyde) and not suitable for commercial manufacture.

The present invention is based on a two-step synthesis of 3-dimethylaminobenzoic acid from 3-nitrobenzoic acid whereby (1) a methanolic solution of one molar proportion of 3-nitrobenzoic acid is reacted with three molar proportions of hydrogen under superatmospheric pressure at a temperature of about 10°–100° C. in the presence of an effective amount of palladium catalyst, optionally in the presence of a minor amount of acetic acid; (2) then, about two molar proportions of formaldehyde are added to the reaction mixture and the reaction continued with an additional two molar proportions of hydrogen under superatmospheric pressure and a temperature of about 15°–100° C. to give 3-dimethylaminobenzoic acid:

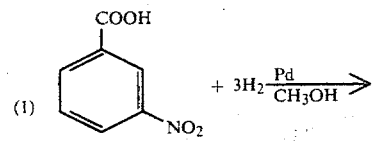

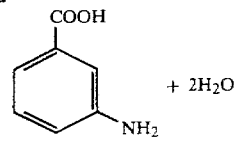

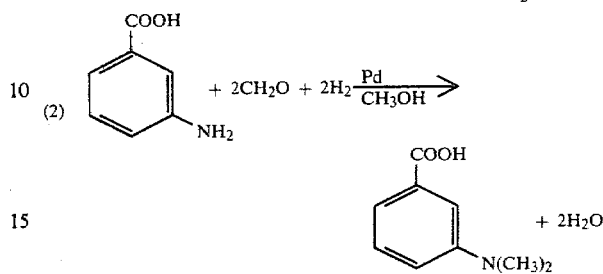

Following the second step, hydrogen gas is vented, the hot solution may be filtered away from the catalyst, and the solution then cooled to recover the 3-dimethylaminobenzoic acid as a crystalline product.

The process of the invention affords high yields (92–93% average) of high purity material and is characterized by (1) the use of methanol as solvent, (2) the use of stoichiometric amounts of formaldehyde, which is withheld until the second step of the reaction, avoiding secondary reactions (3) the use of very small quantities of palladium catalyst, which may be readily re-cycled without regeneration to afford additional high yields of products.

In accordance with the invention, in a first step a suitable pressure vessel, preferably a stirred autoclave equipped for cooling and heating, is charged with methanol and, optionally, a minor amount, e.g., 0.1 to 5.0 percent by weight, based on 3-nitrobenzoic acid, of acetic acid, and an effective amount, generally from about 0.05 to 1.0 percent by weight, same basis, of palladium metal, preferably as a palladium-on-carbon, catalyst. The vessel is purged of oxygen by sweeping several times with an inert gas, e.g., nitrogen, and finally pressurized with hydrogen. Then, a solution of 3-nitrobenzoic acid in methanol is pumped into the reactor, at a rate such as to control the reaction temperature in the range of about 10° to 100° C., preferably 50°–70° C. and most preferably 55° C. to 60° C. The reaction is conducted until the theoretical amount of hydrogen is absorbed.

In a second step, the reactor is again pressurized with hydrogen and a solution of a stoichiometric amount of formaldehyde is added over a period of time sufficient to control the reaction temperature at about 15°–100° C., preferably 50°–70° C., and most preferably at about 55°–60° C. The reaction is continued until the theoretical amount of hydrogen is absorbed. The autoclave is then cooled to about 50° – 55° C., the excess hydrogen is vented, and again pressurized with an inert gas, e.g., nitrogen. The solution is filtered, retaining the catalyst in the reactor, wet with methanol to prevent ignition in air.

The solution of the product may be concentrated by distilling off the methanol and then cooling to about 15° C. to precipitate 3-dimethylaminobenzoic acid, which may be recovered, washed and dried. Overall yield from 3-nitrobenzoic acid is about 92–93% of product having a purity of about 98%.

Sufficient methanol should be used to provide a solution of about 20–25% by weight of 3-nitrobenzoic acid, although the concentration is not critical so long as there is enough methanol to dissolve the 3-nitrobenzoic acid and the product at the temperature of the reaction.

Acetic acid may be added to the reaction mixture, if desired, as a co-catalyst in minor amount, e.g., about 0.1 to 5.0 percent by weight, based on the 3-nitrobenzoic acid. The acetic acid appears to provide some desirable effect in keeping the catalyst surface clean or free from contamination during the reaction.

The palladium catalyst used may be any of the commercially available palladium catalysts, preferably carbon supported palladium. Such catalysts are available containing 3%, 6%, 10% by weight of palladium on a carbon support. An especially preferred catalyst for the present process is a palladium on widepore carbon. These catalysts are described in detail in U.S. Pat. No. 3,978,000 incorporated herein by reference. They comprise a porous, particulate carbon support bonded with a carbonized binder, the carbon black spheres having a particle size of about 80–5000 angstrom units, a pore size distribution exhibiting peaks at a pore radius in excess of 10 angstrom units and a pore volume in the range 0.2–1.0 cubic centimeters per gram. They carry an effective catalytic amount of palladium.

The palladium-on-wide pore carbon catalysts have the advantage of very high activity at very low concentrations of palladium (based on 3-nitrobenzoic acid) and also afford outstanding results when re-cycled without regeneration, i.e., without any special treatment, as shown in the accompanying examples.

When the autoclave containing the methanol, acetic acid and catalyst has been flushed with nitrogen, it is pressurized with hydrogen gas. Then a solution of 3-nitrobenzoic acid in methanol is pumped into the autoclave with cooling to control the reaction temperature since the reaction is exothermic. Three molar proportions of hydrogen are required per molar proportion of 3-nitrobenzoic acid. The reaction is continued until the theoretical amount of hydrogen has been absorbed. The reaction is preferably conducted under at least 20 psi hydrogen pressure and still more preferably above 40 psi hydrogen pressure and maintained at or above the stated pressure until the theoretical amount of hydrogen is absorbed.

The autoclave may then be repressurized with hydrogen. In the second step alkylation of 3-aminobenzoic acid with formaldehyde, two moles of hydrogen are required per mole of 3-aminobenzoic acid. Following the repressurization, formaldehyde is added to the autoclave in any suitable form, but generally as a solution of aqueous formaldehyde, e.g., 37% formalin, or methyl Formcel (54.5% formaldehyde in methanol). The latter is preferred because it minimizes the amount of water in the reaction mixture (a total of 4 moles of water are formed in the reaction) and makes it possible to maintain a higher concentration of the product in solution at the most preferred temperature of about 50°–55° C. The amount of formaldehyde used should be about stoichiometric, i.e., about 2 molar proportions per molar proportion of 3-aminobenzoic acid, though a slight excess may be used.

The reaction is then continued until the theoretical amount of hydrogen is absorbed. The second stage of the reaction is preferably conducted at a pressure of at least about 40 psi hydrogen and still more preferably at a pressure of at least about 80 psi and maintained at or above the stated pressure until the theoretical amount of hydrogen is absorbed. Pressures higher than 100 psi can be used without disadvantages but are not necessary. The autoclave may be then cooled and the hydrogen vented to the atmosphere. The autoclave, which is preferably fitted with a filter, may be pressurized with nitrogen or other inert gas and the reaction mixture filtered, keeping the wet catalyst in the autoclave. The catalyst may then be washed with methanol to remove occluded product and the methanol combined with the solution. The wet catalyst may then be retained in the autoclave for a subsequent batch.

Isolation of the 3-dimethylaminobenzoic acid from solution may be accomplished by any suitable means. The filtrate may be concentrated in volume by distilling methanol and then cooled to below about 15° C. to crystallize the product, which may then be collected, washed and dried.

While the invention has been exemplified by reference to 3-dimethylaminobenzoic acid, it will be understood that the process is applicable to the isomeric 2- and 4- dimethylaminobenzoic acids.

EXAMPLE 1

Preparation of N,N-Dimethylaminobenzoic Acid

A 1-gallon stirred autoclave was charged with 950 ml. methanol, 5 grams of acetic acid and 17.1 grams of 6% palladium-on-wide pore carbon (0.12% palladium, based on 3-nitrobenzoic acid charged). The autoclave was then purged several times with nitrogen and finally with 40 psi hydrogen gas. A solution of 418 grams, 2.5 moles, of 3-nitrobenzoic acid in 850 ml. methanol at room temperature was then pumped into the stirred, cooled autoclave at a rate such that the temperature was controlled in the range 55°–60° C. When the theoretical amount of hydrogen was absorbed (7.5 moles), the hydrogen pressure was increased to 100 psi. A solution of 289 grams of Methyl Formcel (54.5% formaldehyde in methanol; 5.25 moles formaldehyde) was then added over a period of 30 minutes while maintaining the temperature at about 55° C. Hydrogenation was continued for 2–3 hours until the theoretical amount of hydrogen was absorbed (5 moles).

The autoclave was cooled to 50°–55° C., the hydrogen was vented, and then the autoclave was pressurized with 100 psi nitrogen. The reaction mixture was filtered from the catalyst, retaining the wet catalyst in the autoclave. The catalyst was washed with 100 ml. methanol and the wash combined with the filtrate.

The combined filtrate and wash were concentrated by distilling methanol, to a volume of 900 ml. and then cooling to 15° C. to produce a slurry which was filtered. The resulting crystals were washed with 125 ml. methanol in 200 ml. water and dried at 90° C. There was obtained 380 grams (92%) of N,N-dimethylaminobenzoic acid, m.p. 148°–51° C.; purity 98%.

EXAMPLE 2

A 500 ml. glass Parr hydrogenation bottle was charged with 16.7 grams, 0.1 mole, of 3-nitrobenzoic acid dissolved in 95 ml. methanol, 0.3 grams of 3% palladium-on-wide pore carbon, (0.009 gram palladium or 0.054% based on 3-nitrobenzoic acid) and 0.54 grams acetic acid. The bottle was placed in a Parr Rocking Hydrogenation Apparatus and charged with 40 psi hydrogen. When the theoretical amount of hydrogen was absorbed, 16.2 grams of 37% aqueous formaldehyde (0.2 mole) was added and the bottle repressurized to 40 psi with hydrogen. The reaction was complete in a total of 4 hours to give 15.2 grams of N,N-dimethylaminobenzoic acid (92% yield).

The above experiment demonstrates that equivalent results are obtained using aqueous formaldehyde.

EXAMPLES 3-9

Following the procedure of Example 2 a series of experiments were conducted using (A) 6% palladium-on-carbon catalyst (Ex. 3-5) and (B) 6% palladium-on-wide pore carbon (Ex. 6-9). Following the initial experiment, each catalyst was reused as shown in the accompanying table.

The data illustrated the superiority of catalyst (B) over catalyst (A) when re-cycled.

TABLE I

Preparation Of N,N-Dimethylaminobenzoic Acid

| Example | Methanol ml. | Aqueous Formaldehyde, moles | Acetic Acid, moles | Catalyst, Based on m-nitrobenzoic acid | Hydrogen psi | Reaction Time, minutes | Yield % |
|---|---|---|---|---|---|---|---|
| 3 | 130 | 0.2 | 0.009 | (A) 0.138* | 48-39 | 260 | 98 |
| 4 | " | " | 0.008 | recycled | 48-33 | 310 | 56 |
| 5 | " | " | " | " | 48-37 | 315 | 69 |
| 6 | " | " | 0.009 | (B) 0.138* | 47-34 | 260 | 90 |
| 7 | " | " | " | recycled | 47-38 | 150 | 86 |
| 8 | " | " | " | " | 47-39 | 160 | 90 |
| 9 | " | " | " | " | 47-38 | 190 | 90 |

*% palladium based on weight 3-nitrobenzoic acid

EXAMPLE 10

The procedure of Example 2 was followed except that 76 ml. absolute ethanol and 5 ml. concentrated hydrochloric acid (0.06 mole) was substituted for methanol. Hydrogen absorption was very slow. Aqueous formaldehyde was then added (0.2 mole) and the bottle again pressurized with 43 psi hydrogen. In one hour only 25% of the theoretical hydrogen was absorbed and after three hours only 43% of the theoretical amount of hydrogen was absorbed. No product could be obtained from the reaction mixture.

What is claimed is:

1. A process for the manufacture of 3-dimethylaminobenzoic acid which comprises (1) a first step of reacting a methanolic solution of one molar proportion of 3-nitro-benzoic acid with three molar proportions of hydrogen under superatmospheric pressure and at a temperature of about 10°-100° C. in the presence of an effective amount of palladium metal catalyst and optionally from about 0.1 to 5.0 percent by weight, based on the weight of the nitrobenzoic acid of acetic acid; (2) a second step of adding thereto about two molar proportions of formaldehyde and reacting the resulting mixture with an additional two molar proportions of hydrogen under superatmospheric pressure at a temperature of about 15°-100° C.; (3) filtering the resulting methanolic solution of 3-dimethylaminobenzoic acid from the catalyst and recovering 3-dimethylaminobenzoic acid therefrom.

2. The process of claim 1 wherein the palladium catalyst is in the form of palladium-on-carbon.

3. The process of claim 2 wherein said palladium-on-carbon catalyst is a palladium-on-wide pore carbon catalyst; said wide pore carbon characterized as comprised of a porous, particulate carbon support bonded with a carbonized binder, the particulate carbon block spheres having a particle size of about 80-500 angstrom units, a pore size distribution exhibiting peaks at a pore radius in excess of 10 angstrom units and a pore volume in the range of about 0.2-1.0 cubic centimeters per gram.

4. The process of claim 3 wherein said catalyst is washed with methanol following the reaction and recycled to a subsequent batch.

5. The process of claims 1 or 3 wherein said formaldehyde is a solution of formaldehyde in water.

6. The process of claims 1 or 3 wherein said formaldehyde is a solution of formaldehyde in methanol.

7. The process of claims 1 or 3 wherein the temperatures of both the first and second steps are about 50°-70° C.

8. The process of claims 1 or 3 wherein the temperatures of both the first and second steps are about 55°-60° C.

9. The process of claims 1 or 3 wherein the hydrogen pressure of step one is at least 20 psi and of step two at least 40 psi.

10. The process of claims 1 or 3 wherein the hydrogen pressure of step one is at least 40 psi and of step two is at least about 80 psi.

* * * * *